(12) United States Patent
Elkin et al.

(10) Patent No.: US 8,689,797 B2
(45) Date of Patent: *Apr. 8, 2014

(54) MOUTHGUARD FORMED OF PROPYLENE/ALPHA-OLEFIN POLYMER ELASTOMER

(76) Inventors: Monroe Elkin, New Brunswick, NJ (US); Manese Rabeony, Piscataway, NJ (US)

(*) Notice: Subject to any disclaimer, the term of this patent is extended or adjusted under 35 U.S.C. 154(b) by 219 days.

This patent is subject to a terminal disclaimer.

(21) Appl. No.: 13/117,223

(22) Filed: May 27, 2011

(65) Prior Publication Data

US 2012/0325224 A1 Dec. 27, 2012

Related U.S. Application Data (62) Division of application No. 11/128,883, filed on May 13, 2005, now Pat. No. 7,950,394.

(60) Provisional application No. 60/571,325, filed on May 14, 2004, provisional application No. 60/579,539, filed on Jun. 14, 2004.

(51) Int. Cl.
A61C 5/14 (2006.01)

(52) U.S. Cl.
USPC .......................................... 128/861; 523/120

(58) Field of Classification Search
USPC ....... 128/859, 861; 602/902; 433/6; 523/120; 206/63.5, 368
See application file for complete search history.

(56) References Cited

U.S. PATENT DOCUMENTS

| | | |
|---|---|---|
| 3,655,433 A | 4/1972 | Poppe et al. |
| 3,692,025 A | 9/1972 | Greenberg |
| 3,903,059 A | 9/1975 | Johnson et al. |
| 3,984,915 A | 10/1976 | Noble et al. |
| 4,261,373 A | 4/1981 | Tamaoki et al. |
| 4,765,324 A | 8/1988 | Lake, Jr. |
| 4,783,493 A | 11/1988 | Motegi et al. |
| 5,069,953 A | 12/1991 | Kishikawa et al. |
| 5,636,379 A | 6/1997 | Williams |
| 5,769,633 A | 6/1998 | Jacobs et al. |
| 5,863,202 A | 1/1999 | Fontenot et al. |
| 5,931,164 A | 8/1999 | Kiely et al. |
| 6,268,063 B1 | 7/2001 | Kaminaka et al. |
| 6,397,848 B1 | 6/2002 | Kagekata et al. |
| 6,491,036 B2 | 12/2002 | Cook |
| 6,525,157 B2 | 2/2003 | Cozewith et al. |
| 6,635,715 B1 | 10/2003 | Datta et al. |
| 6,642,316 B1 | 11/2003 | Datta et al. |
| 6,768,722 B1 | 7/2004 | Katseff et al. |
| 6,797,378 B2 | 9/2004 | Shimizu |
| 7,175,897 B2 | 2/2007 | Baron et al. |
| 2002/0144695 A1 | 10/2002 | Cook |
| 2004/0038172 A1 | 2/2004 | Jacobs |
| 2004/0149292 A1 | 8/2004 | Fujieda et al. |

Primary Examiner — Patricia Bianco
Assistant Examiner — Camtu Nguyen
(74) Attorney, Agent, or Firm — Porzio, Bromberg & Newman, P.C.

(57) ABSTRACT

A self-customizable dental appliance adapted to lie within the mouth of a person including occlusal pads with a connecting arch or a u-shaped style base with upstanding labial and lingual walls. The appliance is formed of a semi-crystalline polyolefin polymer or crystallizable blend. In one embodiment, the appliance is formed of elastomeric propylene-ethylene polypropylene, optionally including high density polypropylene. An optional occlusal lifting pad can be used in the self-customizable dental appliance.

15 Claims, 5 Drawing Sheets

MOUTHGUARD FORMED OF PROPYLENE/ALPHA-OLEFIN POLYMER ELASTOMER

CROSS-REFERENCE TO RELATED APPLICATION

This application is a divisional of U.S. patent application Ser. No. 11/128,883 filed May 13, 2005, now U.S. Pat. No. 7,950,394, which claims the benefit of U.S. Provisional Patent Application No. 60/571,325 filed May 14, 2004 the entirety of which is hereby incorporated by reference into this application and U.S. Provisional Patent Application No. 60/579,539 filed Jun. 14, 2004 the entirety of which is also hereby incorporated by reference into this application.

BACKGROUND OF THE INVENTION

1. Field of the Invention

The present invention relates to athletic mouthguards and dental appliances, and specifically to self-customizable mouthguards and dental appliances.

2. Description of Related Art

It is known that mouthguards have been used to protect athletes in contact sports from injury to the teeth and also to protect the temporomandibular joint from destructive forces. Recent evidence also indicates that mouthguards may be beneficial in minimizing or preventing concussion. Performance of mouthguards is described in Elkin, M., Increased Athletic Performance using Mouthguards—True or False?, J. New Jersey Dental Assoc., 1996; Stenger, J. M., Mouthguards protection against shock to the head, neck and teeth, J. Am. Dental Assoc., 1964; Duda, M., Which Athletes Should Wear Mouthguards?, Phys. and Sports Med., 1987; and Hickey, J. C., The Relation of mouth protectors to cranial pressure and deformation, J. Am. Dental Assoc., 1967.

Athletes tend to clench their teeth upon exertion. This clenching creates considerable forces on the upper and lower jaws and can lead to damage to the teeth, headaches, neck pain and injury to the temporomandibular joint. Therefore, dental appliances and/or mouthguards have been created to place pads between the upper and lower dentition to prevent this clenching and possible damage to the teeth and other structures.

Historically, mouthguards have been made of ethylene vinyl acetate (EVA). Due to the user clenching and chewing on the appliance, it is subject to degradation. EVA is translucent or white and cannot be made clear. EVA also has a mild ester-like odor and will degrade to hazardous vinyl acetate, acetic acid, carbon monoxide and hazardous hydrocarbon oxidation products. While the mechanical and physical properties of EVA generally fulfill the safety requirements for a custom fitted mouthguard, attempts to mass-produce EVA as a Boil-and-Bite, "do-it-yourself" mouthguard have had limited success and acceptance (see Bishop, B. M., Davis, E. H., von Fraunhoffer, J. A., "Materials for mouth protectors" J. Prosthet. Dent. 1985; 53:256-61 and Chalmers, D. J., "Mouthguards: Protection for mouth in the rugby union" Sports Med. 1998; 25(5):339-49; Winters, Sr., J. E. "Role of properly fitted mouthguards in prevention of sport-related Concussion" J. Athletic Training 2001; 36(3): 339-341). These mouthguards do not fit well and their poor retention plus their lack of proper extension into the buccal vestibule have led Park et al. to state unless dramatic improvements are made, they should not be promoted to customers as they are now (see Park, J. B., Shaull, K. L., Overton, B., Donly, K. I., "Improving mouthguard" J. Prosthet. Dent. 1994; 72: 373-80.

Currently, commercially available mouthguards are (arbitrarily) classified as:

1. Stock over-the-counter—one size fits all. They must be held in place by clenching the teeth together—an obvious contraindication for continuous, vigorous sports requiring unobstructed airways.

2. Boil-and-Bite, mouth formed—these are placed in boiling water and then fitted into the mouth. When athletes attempt to fit these mouthguards, the resulting fit is often inadequate, loose and uncomfortable (see American Society for Testing and Materials. Standard practice for care and use of mouthguards (F 687-80). Reapproved 1992. Philadelphia (PA): American Society for Testing and Materials, 1992).

Attempts been made in engineering EVA for a better fit, comfort and protection; these include sophisticated multilayer composites with a different softening temperature, custom gel fit liner, grip fit technology, or blending EVA with various polymers such as Kraton and polyurethane. (See Kittelsen et al., "Quadruple composite performance enhancing mouthguard" (U.S. Pat. No. 6,675,807); Wagner, E. C. "Custom fit mouthguard" (U.S. Pat. No. 5,566,684); Gel Max Shock Doctor's Mouthguard. www.shockdoc.com; Shock Doctor's 7001 V3.0 Mouthguard. www.shockdoc.com; Shock Doctor's V3 Mouthguard. www.shockdoc.com); and Brett et al., "Mouthguard and method of making" U.S. Pat. No. 6,584,978). Despite these efforts, comfortable custom fitted mouthguards are still difficult to achieve and many athletic trainers and sports participants still prefer the custom-fabricated mouthguards, i.e. from dentist made study casts of the teeth. They are comfortable, fit better with good retention, and allow the user to breathe and speak more easily. Despite the cost, experts in the medical, dental and sports professions are still recommending the custom fitted mouthguard as the best choice and protection (see Chalmers, D. J., "Mouthguards: Protection for mouth in the rugby union" Sports Med. 1998; 25(5):339-49; Winters, Sr., J. E. "Role of properly fitted mouthguards in prevention of sport-related Concussion" J. Athletic Training 2001; 36(3):339-341).

Figure 1:
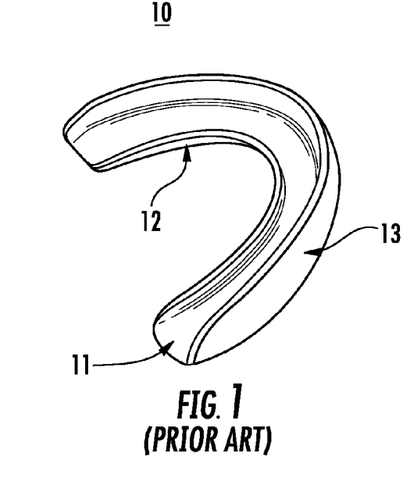
FIG. 1 is a perspective view of a prior art mouthguard made of an elastomer and not designed for a custom fit.

FIG. 1 illustrates a conventional noncustom mouthguard 10 which generally includes a horseshoe or u-shaped base or occlusal pad 11 with a lingual wall 12 and a labial wall 13.

U.S. Pat. No. 6,491,036 discloses a low density polyethylene dental appliance and mouthguard including a nucleating agent. A suitable material is EXACT® from ExxonMobil Chemical Company of Houston, Tex. 77253-3272. This material has ethylene crystallinity which produces a non-elastomeric material with little flexibility or no shrinkage.

There is a need for mouthguards and dental appliances of custom fit without the need to have it formed by a dentist. There is a need for self-customizing dental appliance or mouthguard which is aesthetic, offers protection for the teeth, exhibiting strong tensile strength, high impact properties, flexibility, and have little or no odor.

SUMMARY OF THE INVENTION

The present invention relates to a self-customizable dental appliance comprised of polyolefin-based thermoplastic elastomer. The dental appliance is securely adapted and fitted to the teeth for absorbing forces upon contact with the dental appliance. The dental appliance can have a horseshoe or u-shaped base with an occlusal pad and upstanding labial and lingual walls. A channel between the walls accommodates the teeth of a user. Optionally, the appliance can include a high density material. The use of a high-density material increases the crystalline temperature so that the self-customizable appliance will harden faster for a customized fit.

The self-customizable dental appliance of the present invention exhibits strong tensile strength, high impact properties, flexibility, and has little or no odor. The self-customizable appliance of the present invention can be made clear or colored for identification. The self-customizable appliance of the present invention is nonhazardous. The self-customizable appliance of the present invention can be easily molded by the user of the dental appliance. The self-customizable dental appliance has the advantages of (a) giving the user ample time, (for example, 2 to 3 minutes) to properly fit the mouthguard at a workable temperature below 60° C., during which the material must remain soft and elastic/extensible to conform the contour of the mouth and teeth; (b) providing shrink without any distortion once the mouthguard is comfortably in place; and (c) possessing a good balance of hardness, soft feel and shock absorbing power.

The invention will be more fully described by reference to the following drawings.

DETAILED DESCRIPTION

Reference will now be made in greater detail to a preferred embodiment of the invention, an example of which is illustrated in the accompanying drawings. Wherever possible, the same reference numerals will be used throughout the drawings and the description to refer to the same or like parts.

Figure 2:
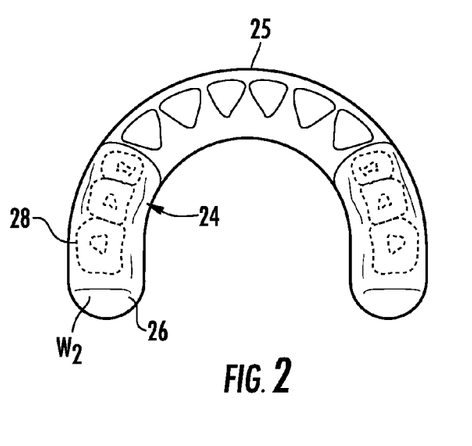
FIG. 2 is a bottom plan view of the self-customizable dental appliance, mouthguard or splint placed on the upper teeth.
Figure 3:
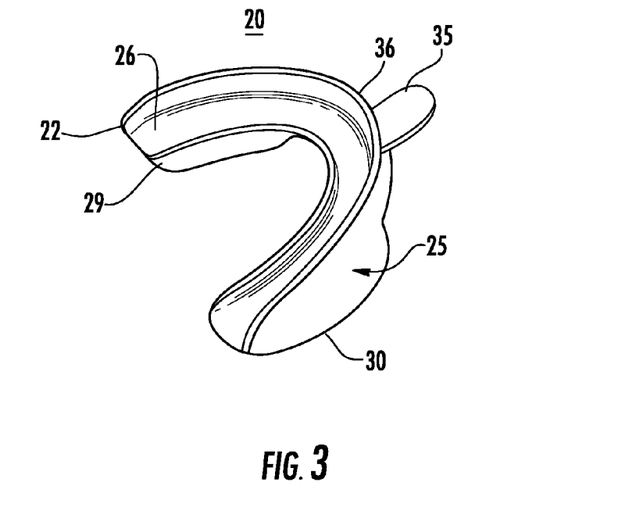
FIG. 3 is a perspective view of the custom fit dental appliance, mouthguard or splint which has been formed to fit the shape of the teeth and gums which has been formed with occlusal posterior pads and a connective arch.
Figure 4:
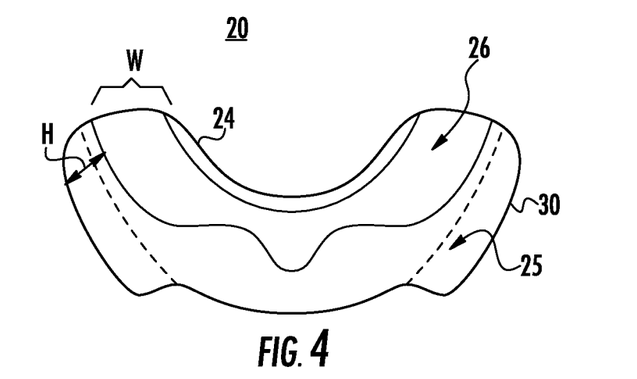
FIG. 4 is a perspective view of a custom fit dental appliance, mouthguard or splint including a channel for teeth.

FIGS. 2 through 4 illustrate dental appliance 20 in accordance with the teachings of the present invention. Dental appliance 20 can be formed as a mouthguard or dental splint. Dental appliance 20 is formed of base 22. Lingual wall 24 and buccal wall 25 extend from base 22. Channel 26 is formed between lingual wall 24 and buccal wall 25. Channel 26 has a width W, which is less than width $W_2$ of teeth 28. For example, channel 26 can have a width in the range of about 1 mm to about 12 mm.

Dental appliance 20 can include a layer of material to form occlusal lifting pad 30. Occlusal lifting pad 30 can have a height in the range of about 3 mm to about 4 mm. Occlusal lifting pad 30 is positioned between the maxilla and mandible adjacent to molars and/or bicuspids for opening the bite of a user.

Dental appliance 20 is formed of a material which is self-customizable by a user of dental appliance 20. Dental appliance 20 can be formed of a semi-crystalline polyolefin polymer or polymer blend. Suitable polyolefin polymers include propylene-ethylene copolymer. The semi-crystalline polymer can be a thermoplastic polymer. The semi-crystalline polyolefin polymer can have low density. Suitable polymers for forming dental appliance 20 can include low density polypropylene. Optionally, a high density polypropylene can be used with the low density polyolefin.

Suitable polyolefin polymers include propylene-ethylene copolymers produced in the presence of a metallocene catalyst and activator as described in U.S. Pat. No. 6,525,157 hereby incorporated by reference into this application. The copolymer can comprise about 5 to 25% by weight of ethylene-derived units and about 55 to 75% by weight of propylene derived units.

The semi-crystalline propylene ethylene copolymer is formed by copolymerizing propylene-ethylene copolymer.

Suitable thermoplastic polymer blends comprise a composition formed of an isotatic polypropylene component and an alpha olefin and propylene copolymer, the copolymer comprising crystallizable alpha olefin sequences as described in U.S. Pat. No. 6,635,715 and U.S. Pat. No. 6,642,316 hereby each incorporated by reference into this application. The composition can be formed by blending at least a first polymer component and a second polymer component, the blend comprising: from about 2% to about 95% by weight of the first polymer component, the first polymer component comprising isotactic polypropylene and having a melting point greater than about 110° C., and copolymerizing propylene and ethylene using a chiral metallocene catalyst system, the copolymer having crystallinity from about 2% to about 65% from isotactic polypropylene sequences, a propylene content of from about 75% to about 90% by weight, a melting point of from 50° C. to 105° C., and wherein a glass transition temperature of the second polymer component is retained in the polymer blend. Alternatively, the polymer blend can be an uncrosslinked blend composition comprising a dispersed phase of a crystalline polymer component in a continuous phase of a crystallizable polymer component wherein: a) the crystalline polymer component is dispersed in phases less than 3 µm×3 µm×100 µm in size, b) the blend composition has greater than 65% propylene units by weight, c) the blend comprises greater than 1% but less than 40% by weight is based on the total weight of the blend of a crystalline first polymer component and less than 99% but greater than 60% by weight based on the total weight of the blend of a crystallizable second polymer component, such crystallinity being due to stereoregular polymerized propylene units, d) both first and second polymer component contain stereoregular polymerized propylene units of identical tacticity, e) the blend has a tensile elongation greater than 650%, wherein the first polymer component is a propylene homopolymer and has a melting point by DSC equal to or above 115° C., and the second polymer component is a copolymer of the propylene units and from about 8% to about 25% by weight ethylene units and has a melting point equal to or less than about 100° C.

A suitable material is Vistamaxx from ExxonMobil Chemical Company of Houston, Tex. 77253-3272.

Other polymers can be blended or laminated with the propylene-ethylene copolymer to provide enhanced properties. For example, suitable polymers can include elastomers, plastomers, and rubber.

Colorants can be added to the propylene-ethylene copolymer to achieve a suitable aesthetic appearance. For example, the colorants can be clear. A suitable colorant is sold by Milliken Chemical under the trade designation CLEARTINT® (Milliken Chemical Division of Milliken & Company (Spartanburg, S.C.)). Light reflective material can also be added or attached to the propylene-ethylene copolymer to achieve additional aesthetic appearance.

A method forming a self-customizable dental appliance comprises the steps of placing the dental appliance 20 in a hot medium. For example, after molding into dental appliance 20, the user simply places dental appliance 20 into a hot liquid, for example, dental appliance 20 can be placed into water having a temperature of about 60° C. to about 100° C. for a few seconds. The appliance is then removed and self-customized to the user's mouth, teeth and gums to provide a custom fit. Alternatively, dental appliance 20 can be placed in a wet paper towel and heated in a microwave oven. For example, dental appliance 20 can be heated for about 30 seconds to about 90 seconds in a microwave oven on a high setting. In one example, dental appliance 20 can be heated for about 60 seconds in a microwave on a high setting. Dental appliance 20 can be cooled for a short period of time, for example about 5 seconds. After placing dental appliance 20 in the mouth for customizing, dental appliance 20 can be left in the mouth until comfortable or placed in cold water for two minutes and returned to the mouth.

Dental appliance 20 can have a height of H, which is substantially the height of teeth 28, and after molding, dental appliance can be retained against teeth 28 due to the self-customizable fit.

In one embodiment, dental appliance 20 can be used as temporomandibular joint (TMJ) bruxism appliance, as shown in FIG. 4.

Figure 5:
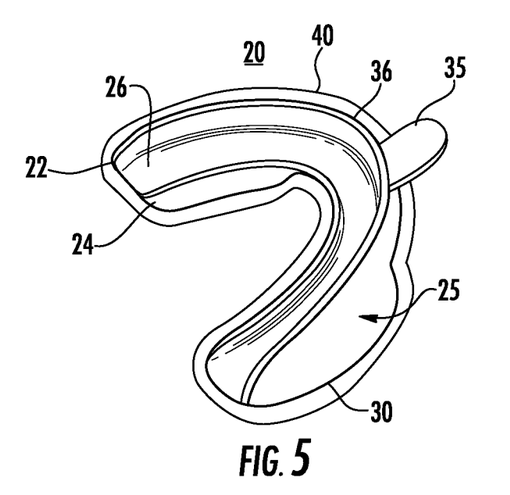
FIG. 5 is a perspective view of a custom fit dental appliance, mouthguard or splint including a channel for teeth including a fit lock appliance.

In an embodiment, fit lock 40 is positioned over dental appliance 20 after placement of dental appliance 20 in the user's mouth, as shown in FIG. 5. Fit lock 40 holds and locks dental appliance 20 in the self-customizable shape during cooling of dental appliance 20. Fit lock 40 can have a slightly larger dimension to fit over dental appliance 20. For example, fit lock 40 can be formed of plastic.

Figure 6:
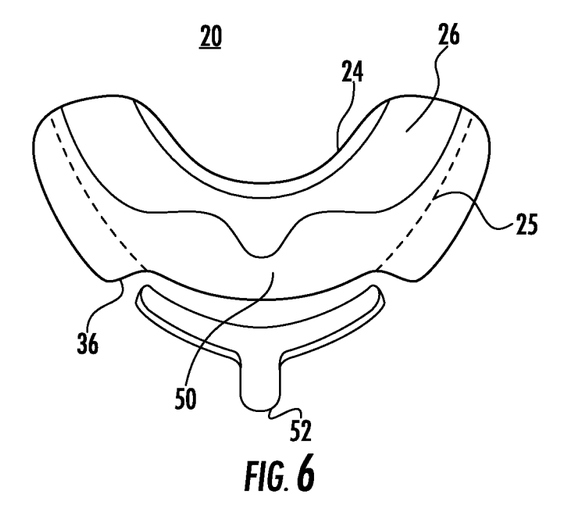
FIG. 6 is a perspective view of a custom fit dental appliance, mouthguard or splint including a tether.

In an embodiment of the present invention, tether 50 is attached to dental appliance 20, as shown in FIG. 6. For instance, tether 50 can extend from front 36 of dental appliance 20. Tether 50 can be used for removing dental appliance 20 from the hot medium or a microwave oven. In one embodiment, tether 50 of dental appliance 20 can be used to attach to a face mask of a helmet. Alternatively, tether 50 can be removed from dental appliance 20 before use.

Figure 7:
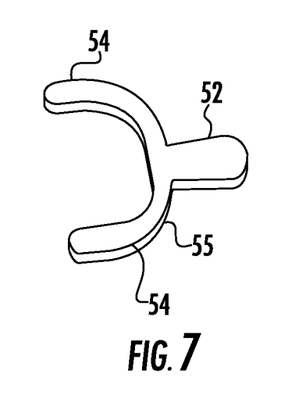
FIG. 7 is a perspective view of an anterior spacer and handle.

In an alternate embodiment, handle 52 can be coupled to front 36 of dental appliance 20. Anterior spacer 54 can be coupled to bottom portion 55 of handle 52. Anterior spacer 54 can have a height of about 3 mm to about 4 mm.

Figure 8:
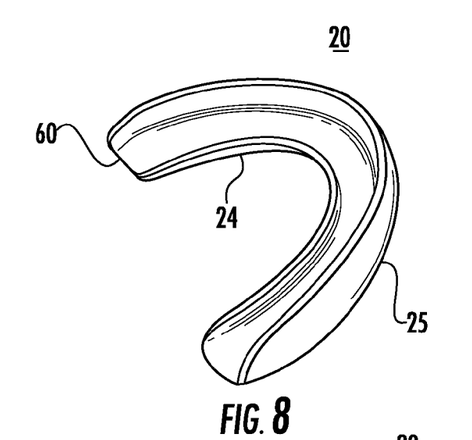
FIG. 8 is a perspective view of a dental appliance of a bleaching tray including a liner.

In an alternate embodiment, dental appliance 20 can be used as a bleaching tray, as shown in FIG. 8. Dental appliance 20 includes liner 60. Liner 60 can be used for absorption of a bleaching material 62.

Figure 9:
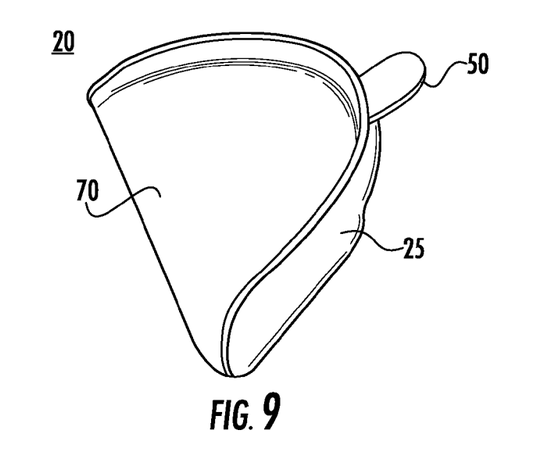
FIG. 9 is a perspective view of a dental appliance of an upper impression tray.

In an alternate embodiment, dental appliance 20 is formed as an upper impression tray, as shown in FIG. 9. Dental appliance 20 comprises full palatal pad 70 and buccal wall 25. Handle 74 extends from front 36 of dental appliance 20.

Figure 10:
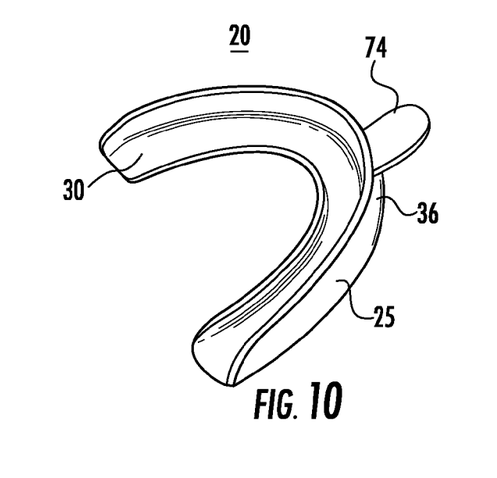
FIG. 10 is a perspective view of a dental appliance of a lower impression tray.

In an alternate embodiment, dental appliance 20 is formed as a lower impression tray, as shown in FIG. 10. Lower impression tray comprises buccal wall 25 and occlusal lifting pad 30. The upper impression tray and lower impression tray can be used for taking impressions.

Dental appliance 20 has improved shrinkage to product a custom fit in comparison with EVA mouthguards. Dental appliance 20 has increased overall fitting time in comparison with EVA mouthguards.

The following Example is illustrative of the present invention as described in the claims which follow thereafter:

EXAMPLE

Dental appliance 20 was made from a thermoplastic polyolefin elastomer referred to as Vistamaxx™ which is manufactured by ExxonMobil Chemical. Table 1 compares the physical and mechanical property range of Vistamaxx with a mouthguard formed of EVA 28% vinyl acetate. The results show that the physical and mechanical properties match or surpass EVA. Dental appliance 20 provides a greater rate of crystallization or fitting time, i.e., the time interval before the material stiffens at body temperature. EVA hardens within 10 to 20 seconds. Any attempt to fit the mouthguard within this time interval results in an ill-fitted mouthguard with poor retention. Dental appliance 20 takes 2 to 3 minutes for the mouthguard to harden. This gives the user ample time to properly fit the mouthguard. During this time interval, the material remains soft and extensible. In addition, the high shrinkage of dental appliance 20 allows the mouthguard to shrink, giving a snug fit with excellent retention to the teeth and jaw within 5 minutes.

TABLE I

| Physical and Mechanical Properties | Dental Appliance 20 | Conventional Mouthguard EVA (28% Vinyl acetate) |
| --- | --- | --- |
| Density, g/cc | 0.86-0.89 | 0.95 |
| Melting Point ° C. | 55-160 | 70 |
| Tensile Strength (psi) | 2200-4500 | 2100 |
| Die C Tear Strength (ibf/in) | 130-330 | 250 |
| Elongation at Break (%) | 100-1500 | 800 |
| Flexural Modulus (psi)) | 1500-6500 | 2300 |
| Hardness (Shore A) | 50-90 | 80 |
| Shrinkage to teeth | Excellent | Poor |
| Overall fitting time | 2-3 minutes | 10-20 seconds |

It is to be understood that the foregoing description and specific embodiments are merely illustrative of the best mode of the invention and the principles thereof. Various modifications and additions may be made to the present invention by those skilled in the art without departing from the spirit and scope of this invention which is to be limited only by the scope of the appended claims.

What is claimed is:

1. A self-customizable dental appliance formed of a semi-crystalline propylene ethylene copolymer comprising about 5% to about 25% by weight of ethylene-derived units and about 55% to about 95% by weight of propylene, wherein said semi-crystalline propylene ethylene copolymer is formed by copolymerizing propylene and ethylene using a chiral metallocene catalyst system, said semi-crystalline propylene-ethylene copolymer having crystallinity from about 2% to about 65% from polypropylene sequences, wherein said dental appliance is adapted to securely fit to teeth and wherein said dental appliance is configured to be molded by heating to a temperature of about 60° C. to about 100° C. and said dental appliance remains elastic/extensible at a workable temperature below 60° C. to conform said dental appliance to the contour of the mouth and teeth further comprising a layer of material extending upwardly in height, wherein said layer of material is adapted to be positioned adjacent to molars and/or bicuspids.

2. The self-customizable dental appliance of claim 1 wherein said layer of material has a height in the range of about 3 mm to about 4 mm.

3. A self-customizable dental appliance formed of a semi-crystalline propylene ethylene copolymer comprising about 5% to about 25% by weight of ethylene-derived units and about 55% to about 95% by weight of propylene, wherein said semi-crystalline propylene ethylene copolymer is formed by copolymerizing propylene and ethylene using a chiral metallocene catalyst system, said semi-crystalline propylene-ethylene copolymer having crystallinity from about 2% to about 65% from polypropylene sequences, wherein said dental appliance is adapted to securely fit to teeth and wherein said dental appliance is configured to be molded by heating to a temperature of about 60° C. to about 100° C. and said dental appliance remains elastic/extensible at a workable temperature below 60° C. to conform said dental appliance to the contour of the mouth and teeth further comprising:
a colorant added to said semi-crystalline propylene ethylene copolymer.

4. The self-customizable dental appliance of claim 3 wherein the colorant is clear.

5. A self-customizable dental appliance formed of a semi-crystalline propylene ethylene copolymer comprising about 5% to about 25% by weight of ethylene-derived units and about 55% to about 95% by weight of propylene, wherein said semi-crystalline propylene ethylene copolymer is formed by copolymerizing propylene and ethylene using a chiral metallocene catalyst system, said semi-crystalline propylene-ethylene copolymer having crystallinity from about 2% to about 65% from polypropylene sequences, wherein said dental appliance is adapted to securely fit to teeth and wherein said dental appliance is configured to be molded by heating to a temperature of about 60° C. to about 100° C. and said dental appliance remains elastic/extensible at a workable temperature below 60° C. to conform said dental appliance to the contour of the mouth and teeth further comprising:
a light reflective material added to said semi-crystalline polyolefin polymer or crystallizable polymer or blend.

6. A self-customizable dental appliance formed of a semi-crystalline propylene ethylene copolymer comprising about 5% to about 25% by weight of ethylene-derived units and about 55% to about 95% by weight of propylene, wherein said semi-crystalline propylene ethylene copolymer is formed by copolymerizing propylene and ethylene using a chiral metallocene catalyst system, said semi-crystalline propylene-ethylene copolymer having crystallinity from about 2% to about 65% from polypropylene sequences, wherein said dental appliance is adapted to securely fit to teeth and wherein said dental appliance is configured to be molded by heating to a temperature of about 60° C. to about 100° C. and said dental appliance remains elastic/extensible at a workable temperature below 60° C. to conform said dental appliance to the contour of the mouth and teeth further comprising a fit lock appliance, said fit lock appliance fitting over said upstanding wall and said one or more channels of said dental appliance during molding of said dental appliance, said fit lock having a slightly larger dimension than said dental appliance.

7. The self-customizable dental appliance of claim 6 wherein said fit lock is formed of plastic.

8. The self-customizable dental appliance of claim 7 further comprising an anterior spacer extending from a bottom portion of a handle.

9. A self-customizable dental appliance formed of a semi-crystalline propylene ethylene copolymer comprising about 5% to about 25% by weight of ethylene-derived units and about 55% to about 95% by weight of propylene, wherein said semi-crystalline propylene ethylene copolymer is formed by copolymerizing propylene and ethylene using a chiral metallocene catalyst system, said semi-crystalline propylene-ethylene copolymer having crystallinity from about 2% to about 65% from polypropylene sequences, wherein said dental appliance is adapted to securely fit to teeth and wherein said dental appliance is configured to be molded by heating to a temperature of about 60° C. to about 100° C. and said dental appliance remains elastic/extensible at a workable temperature below 60° C. to conform said dental appliance to the contour of the mouth and teeth further comprising a handle extending from a front of said dental appliance.

10. A self-customizable dental appliance formed of a semi-crystalline propylene ethylene copolymer comprising about 5% to about 25% by weight of ethylene-derived units and about 55% to about 95% by weight of propylene, wherein said semi-crystalline propylene ethylene copolymer is formed by copolymerizing propylene and ethylene using a chiral metallocene catalyst system, said semi-crystalline propylene-ethylene copolymer having crystallinity from about 2% to about 65% from polypropylene sequences, wherein said dental appliance is adapted to securely fit to teeth and wherein said dental appliance is configured to be molded by heating to a temperature of about 60° C. to about 100° C. and said dental appliance remains elastic/extensible at a workable temperature below 60° C. to conform said dental appliance to the contour of the mouth and teeth wherein said dental appliance is a dental splint.

11. A self-customizable dental appliance formed of a semi-crystalline propylene ethylene copolymer comprising about 5% to about 25% by weight of ethylene-derived units and about 55% to about 95% by weight of propylene, wherein said semi-crystalline propylene ethylene copolymer is formed by copolymerizing propylene and ethylene using a chiral metallocene catalyst system, said semi-crystalline propylene-ethylene copolymer having crystallinity from about 2% to about 65% from polypropylene sequences, wherein said dental appliance is adapted to securely fit to teeth and wherein said dental appliance is configured to be molded by heating to a temperature of about 60° C. to about 100° C. and said dental appliance remains elastic/extensible at a workable temperature below 60° C. to conform said dental appliance to the contour of the mouth and teeth wherein said dental appliance is a temporomandibular joint bruxism appliance.

12. A self-customizable dental appliance formed of a semi-crystalline propylene ethylene copolymer comprising about 5% to about 25% by weight of ethylene-derived units and about 55% to about 95% by weight of propylene, wherein said semi-crystalline propylene ethylene copolymer is formed by copolymerizing propylene and ethylene using a chiral metallocene catalyst system, said semi-crystalline propylene-ethylene copolymer having crystallinity from about 2% to about 65% from polypropylene sequences, wherein said dental appliance is adapted to securely fit to teeth and wherein said dental appliance is configured to be molded by heating to a temperature of about 60° C. to about 100° C. and said dental appliance remains elastic/extensible at a workable temperature below 60° C. to conform said dental appliance to the contour of the mouth and teeth wherein said dental appliance is a bleaching appliance.

13. A self-customizable dental appliance formed of a semi-crystalline propylene ethylene copolymer comprising about 5% to about 25% by weight of ethylene-derived units and about 55% to about 95% by weight of propylene, wherein said semi-crystalline propylene ethylene copolymer is formed by copolymerizing propylene and ethylene using a chiral metallocene catalyst system, said semi-crystalline propylene-ethylene copolymer having crystallinity from about 2% to about 65% from polypropylene sequences, wherein said dental appliance is adapted to securely fit to teeth and wherein said dental appliance is configured to be molded by heating to a temperature of about 60° C. to about 100° C. and said dental appliance remains elastic/extensible at a workable temperature below 60° C. to conform said dental appliance to the contour of the mouth and teeth further comprising a liner for receiving a bleaching composition.

14. A self-customizable dental appliance formed of a semi-crystalline propylene ethylene copolymer comprising about 5% to about 25% by weight of ethylene-derived units and about 55% to about 95% by weight of propylene, wherein said semi-crystalline propylene ethylene copolymer is formed by copolymerizing propylene and ethylene using a chiral metallocene catalyst system, said semi-crystalline propylene-ethylene copolymer having crystallinity from about 2% to about 65% from polypropylene sequences, wherein said dental appliance is adapted to securely fit to teeth and wherein said dental appliance is configured to be molded by heating to a temperature of about 60° C. to about 100° C. and said dental appliance remains elastic/extensible at a workable temperature below 60° C. to conform said dental appliance to the contour of the mouth and teeth wherein the dental appliance is an upper impression tray including a full palatal.

15. A self-customizable dental appliance formed of a semi-crystalline propylene ethylene copolymer comprising about 5% to about 25% by weight of ethylene-derived units and about 55% to about 95% by weight of propylene, wherein said semi-crystalline propylene ethylene copolymer is formed by copolymerizing propylene and ethylene using a chiral metallocene catalyst system, said semi-crystalline propylene-ethylene copolymer having crystallinity from about 2% to about 65% from polypropylene sequences, wherein said dental appliance is adapted to securely fit to teeth and wherein said dental appliance is configured to be molded by heating to a temperature of about 60° C. to about 100° C. and said dental appliance remains elastic/extensible at a workable temperature below 60° C. to conform said dental appliance to the contour of the mouth and teeth wherein the dental appliance is a lower impression tray.

* * * * *